United States Patent [19]

Ohkawa et al.

[11] Patent Number: 5,708,005
[45] Date of Patent: Jan. 13, 1998

[54] QUINOLINES, THEIR PRODUCTION AND USE

[75] Inventors: Shigenori Ohkawa, Takatsuki; Osamu Uchikawa, Kobe; Masaomi Miyamoto, Takarazuka, all of Japan

[73] Assignee: Takeda Chemical Industries, Ltd., Osaka, Japan

[21] Appl. No.: 718,430

[22] PCT Filed: Jun. 26, 1996

[86] PCT No.: PCT/JP96/01759

§ 371 Date: Dec. 10, 1996

§ 102(e) Date: Dec. 10, 1996

[87] PCT Pub. No.: WO97/01539

PCT Pub. Date: Jan. 16, 1997

[30] Foreign Application Priority Data

Jun. 27, 1995 [JP] Japan .................. 7-161114

[51] Int. Cl.$^6$ .................. C07D 215/12; C07D 215/16; C07D 215/60; A61K 31/47
[52] U.S. Cl. .................. 514/311; 514/291; 514/312; 546/90; 546/153; 546/175
[58] Field of Search .................. 546/153, 175, 546/90; 514/34, 312, 291

[56] References Cited

U.S. PATENT DOCUMENTS

| | | | |
|---|---|---|---|
| 3,615,889 | 10/1971 | Rauch | 428/470 |
| 4,578,381 | 3/1986 | Uchida et al. | 514/233 |
| 5,194,614 | 3/1993 | Andrieux et al. | 544/400 |
| 5,342,947 | 8/1994 | Lackey et al. | 546/41 |
| 5,464,872 | 11/1995 | Langlois et al. | 514/630 |
| 5,552,418 | 9/1996 | Depreux et al. | 514/348 |

FOREIGN PATENT DOCUMENTS

| | | |
|---|---|---|
| 0373891 | 6/1990 | European Pat. Off. . |
| 0447285 | 9/1991 | European Pat. Off. . |
| 0540099 | 5/1993 | European Pat. Off. . |
| 0556585 | 8/1993 | European Pat. Off. . |
| 0591057 | 4/1994 | European Pat. Off. . |
| 0662471 | 7/1995 | European Pat. Off. . |
| 0680967 | 11/1995 | European Pat. Off. . |
| 680967 | 11/1995 | European Pat. Off. . |
| 0721938 | 7/1996 | European Pat. Off. . |
| 721938 | 7/1996 | European Pat. Off. . |
| 60-142959 | 7/1985 | Japan . |
| WO 13871 | 9/1991 | WIPO . |
| WO 07856 | 5/1992 | WIPO . |
| WO 03433 | 2/1994 | WIPO . |
| WO 07487 | 4/1994 | WIPO . |
| WO 08466 | 3/1996 | WIPO . |
| WO 21666 | 7/1996 | WIPO . |

OTHER PUBLICATIONS

John, Chem. Berichte, vol. 58 (1925) 2804–5 (English Translation).
Int. J. Peptide Protein Res., 38, (1991) 218–228.
Arch. Pharm. Ber. Deut. Pharm. Ges., 305(4) (1972) 244–248.
Chemical Abstracts, vol. 76, No. 15 (Apr. 1972) 85667q.
Chemical Abstracts, vol. 79, No. 9 (Sep. 1973) 52563m.
Chemical Abstracts, vol. 84, No. 9 (Mar. 1976) 59237v.
Chemical Abstracts, vol. 102, No. 11 (Mar. 1985) 95511d.
Chemical Abstracts, vol. 104, No. 11 (Mar. 1986) 88454a.
Kingsbury et al., J. Med. Chem., vol. 34, No. 1 (Jan. 1991) 98–107.
Chemical Abstracts, vol. 119, No. 21 (Nov. 1993) 225779m.
Bioorganic & Medicinal Chemistry Letters, vol. 4, No. 12 (1994) 1485–90.
White et al., J. Am. Chem. Soc., vol. 116, No. 5 (Mar. 1994) 1831–38.
Gellerman et al., Tetrahedron, vol. 50, No. 45 (1994) 12959–72.
H. John, Chmische Berichte, vol. 58 (1925) 2799–2805.
Miki et al., J. Chem. Soc. (1933) 1467–69.
Walker, J. Chem. Soc. (1947) 1684–87.
Chemical Abstracts, vol. 84, No. 23 (Jun. 1976) 163786j.
Chemical Abstracts, vol. 95, No. 13 (Sep. 1981) 115240g.
Chemical Abstracts, vol. 114, No. 17 (Apr. 1991) 164085e.
Yous et al., J. Med. Chem., vol. 35, No. 8 (Apr. 1992) 1484–86.
Depreux et al., J. Med. Chem., vol. 37, No. 20 (Sep. 1994) 3231–39.

*Primary Examiner*—Alan L. Rotman
*Assistant Examiner*—D. Margaret M. Mach
*Attorney, Agent, or Firm*—Fitzpatrick, Cella, Harper & Scinto

[57] ABSTRACT

A compound of the formula:

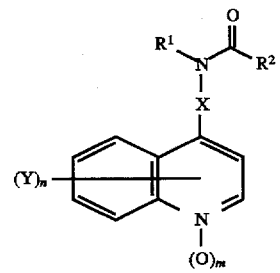

wherein $R^1$ represents hydrogen or an optionally substituted hydrocarbon group; $R^2$ represents an optionally substituted hydrocarbon group, an optionally substituted amino group or a substituted hydroxyl group; X represents an optionally halogenated lower alkylene group; Y represents a substituent; n represents an integer of 0 to 6; and m represents 0 or 1; or a salt thereof, a process for producing it, an intermediate for the production, and a pharmaceutical composition containing it are provided.

17 Claims, No Drawings

QUINOLINES, THEIR PRODUCTION AND USE

This application is a 371 of PCT/JP96/01759, filed 26 Jun. 1996.

TECHNICAL FIELD

The present invention relates to a novel quinoline compound having an excellent binding affinity for melatonin receptor, a process for producing it, an intermediate for the production and a composition containing it.

BACKGROUND ART

Melatonin (N-acetyl-5-methoxytryptamine), which is a hormone that is synthesized and secreted principally in the pineal gland, increases in dark circumstances and decreases in light circumstances. Further, melatonin exerts suppressively on pigment cells or female gonad and acts as a synchronous factor of biological clock while taking part in transmittance of photoperiodic code. Therefore, melatonin is expected to be used for therapy of diseases related with melatonin activity, such as reproduction and endocrinic disorders, sleep-awake rhythm disorders, jet lag syndrome and various aging disorders.

Recently it was reported in Ann. N.Y. Acad. Sci., Vol. 719, PP. 456–460 (1994) that the production of melatonin decline steadily into old age and the supplementing melatonin could reset the body's aging clock. However, in "Bioorganic & Medicinal Chemistry Letters, Vol. 4, p. 1485 (1994)", there is described that melatonin is shown to be inactive on central nervous system when administered peripherally because melatonin itself has poor intracerebral transferability. In addition, it is reported that melatonin is readily metabolized by metabolic enzymes in a living body (Rinsho Kensa, Vol. 38, No. 11 (1994)). For these reasons, melatonin agonist which has a different structure from melatonin, has stronger activities than melatonin, is metabolically stable, has excellent transferability into brain, and can be expected to show superior therapeutic effects to those of melatonin.

As a melatonin agonist, naphthalene derivatives having an acylaminoethyl group at the 1-position, N-[2-(7-methoxynapht-1-yl)ethyl]acetamide, etc., have been reported (EP-A-447285, JP-A 7-48331). As a melatonin agonist, a melatonin derivative having an indole skeleton (EP-A-578620, JP-A 6-72874, etc.), a tetrahydronaphthalene derivative having an acylamino group at the 2-position (EP-A-420064, JP-A 3-169840, etc.), etc., have been reported. However, no melatonin agonistic or antagonistic compound having a quinoline skeleton has been known.

As compounds having a quinoline skeleton, a compound of the formula:

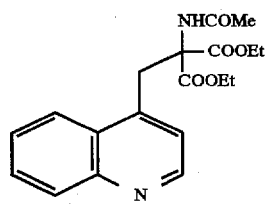

having gramicidin channel activity is disclosed in International Journal of Peptide and Protein Research, Vol. 38, PP 218–228 (1991).

Also, a compound of the formula:

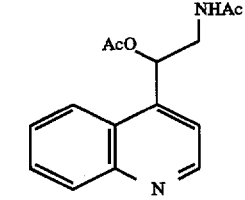

wherein $R^0$ is H, etc., $R^1$ is H, etc., $R^2$ is H, halogens, etc., $R^3$ is hydroxyl, lower alkoxy, etc., $R^4$ is H, —$COR^5$, etc., $R^5$ is lower alkyl, etc., A is lower alkylene, and n is 0 or 1, having anti-ulcer activity, is disclosed in U.S. Pat. No. 4,578,381.

Additionaly, a compound of the formula:

having β-blocker activity is disclosed in Archiv der Pharmazie und Berichte der Deutschen Pharmazeutischen Gesellschaft Vol. 305 (4), PP 244–248 (1972).

However, not one of these references refers to melatonin receptor affinities.

A melatonin agonist, which is different from melatonin in the structure, has an excellent affinity for melatonin receptor, is metabolically stable and is excellent in the transferability into brain, can be expected to show superior therapeutic effects to those of melatonin. And, when the antagonistic activities of melatonin are desired, creation of a new melatonin antagonist is necessary.

At the present circumstances, no compound which are fully satisfactory in the activities of melatonin receptors, in metabolical stability and in transferability into brain have been found. So, development of compounds, which are different from the above-mentioned known compounds in chemical structure, have excellent melatonin receptor affinities and are fully satisfactory as medicines, is ardently desired.

DISCLOSURE OF INVENTION

The present inventors have firstly succeeded in creation of a novel quinoline compound characterized by an acylamino (halogeno)lower alkyl group at the 4-position of the quinoline skeleton, and found that such compound exhibits excellent affinity for melatonin receptors and stability as melatonin agonists and, accordingly, is satisfactory as a therapeutics. Based on these findings, the present inventors have completed the invention.

The present invention relates to (1) a compound of the formula (I):

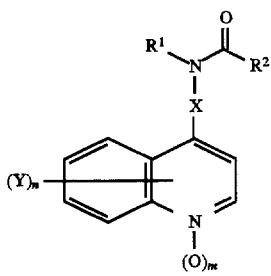

wherein $R^1$ represents hydrogen or an optionally substituted hydrocarbon group;

$R^2$ represents an optionally substituted hydrocarbon group, an optionally substituted amino group or a substituted hydroxyl group;

X represents an optionally halogenated lower alkylene group;

Y represents a substituent;

n represents an integer of 0 to 6; and m represents 0 or 1;

or a salt thereof, (2) the compound of the above (1) wherein $R^1$ is i) hydrogen or ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, $R^2$ is i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, or iii) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl or $C_{6-10}$ aryloxy, X is a straight or branched $C_{1-6}$ alkylene group optionally substituted by 1 to 5 halogens, and Y is i) halogen, ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, iii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, iv) a mercapto group which may be substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl or $C_{6-10}$ aryloxy, v) hydroxy, vi) $C_{1-6}$ alkoxy, vii) $C_{1-6}$ acylamino or viii) $C_{1-3}$ alkylenedioxy, (3) the compound of the above (2) wherein X is an ethylene group, (4) the compound of the above (2) wherein $R^2$ is a $C_{1-6}$ alkyl or $C_{3-6}$ cycloalkyl group optionally substituted by 1 to 5 halogens, (5) the compound of the above (1) wherein the 6-position on the quinoline ring is substituted by a $C_{1-6}$ alkoxy group, (6) the compound of the above (2) wherein $R^1$ is hydrogen or $C_{1-6}$ alkyl, $R^2$ is a $C_{1-6}$ alkyl or $C_{3-6}$ cycloalkyl group optionally substituted by 1 to 3 halogens, X is an ethylene group, Y is i) halogen, ii) a $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, iii) a $C_{1-6}$ alkoxy group or iv) a $C_{1-6}$ alkyl group, n is an integer of 1 to 3 and m is 0, (7) the compound of the above (1) which is a compound of the formula:

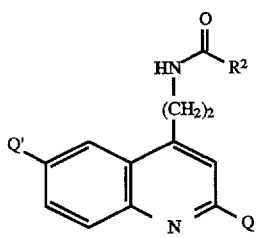

wherein $R^2$ is a $C_{1-6}$ alkyl or $C_{1-6}$ cycloalkyl group optionally substituted by 1 to 3 halogens, Q is hydrogen, halogen, a $C_{6-14}$ aryl group or a $C_{1-6}$ alkoxy group and Q' is a $C_{1-6}$ alkoxy group, or a salt thereof, (8) the compound of the above (1) which is
N-[2-(2-chloro-6-methoxyquinolin-4-yl)ethyl]acetamide,
N-[2-(6-methoxyquinolin-4-yl)ethyl]acetamide,
N-[2-(2-chloro-6-methoxyquinolin-4-yl)ethyl]-2,2,2-trifluoroacetamide,
N-[2-(6-methoxyquinolin-4-yl)ethyl]-2,2,2-trifluoroacetamide,
N-[2-(2-chloro-6-methoxyquinolin-4-yl)ethyl] propionamide,
N-[2-(6-methoxyquinolin-4-yl)ethyl]propionamide, or a salt thereof, (9) a process for producing the compound of the above 1, which comprises subjecting a compound of the formula:

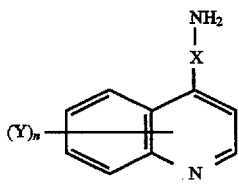

wherein all symbols are as defined above or a salt thereof to acylation or reaction with an isocyanate, and if necessary, subjecting the resultant compound to oxidation and/or substituent-exchange reaction,

(10) a compound of the formula:

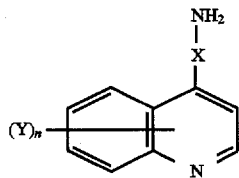

wherein all symbols are as defined above, or a salt thereof,

(11) a pharmaceutical composition which comprises a compound of the above (1), if necessary together with a pharmaceutically acceptable carrier,

(12) the composition of the above (11) which has a binding affinity for melatonin receptor,

(13) the composition of the above (12) which is a regulating agent of circadian rhythm,

(14) the composition of the above (12) which is a regulating agent of sleep-awake rhythm,

(15) the composition of the above (12) which is a regulating agent of time zone change syndrome (or desynchronization syndrome),

(16) the composition of the above (11) which is a therapeutic agent of sleep disorders,

(17) method for treating or preventing disease related to the action of melatonin in mammals which comprises administering to a subject in need a therapeutically effective amount of a compound of the above (1) and a pharmaceutically acceptable carrier, and

(18) use of a compound of the above (1) for manufacturing a pharmaceutical composition for treating or preventing diseases relating to the action of melatonin in mammals.

"Hydrocarbon group" of "optionally substituted hydrocarbon group" represented by $R^1$ or $R^2$ include, among others, aliphatic hydrocarbon groups, monocyclic saturated hydrocarbon groups and aromatic hydrocarbon groups. The carbon number of the hydrocarbon group is preferably 1 to 16. An alkyl group, an alkenyl group, an alkynyl group, a cycloalkyl group and an aryl group are exemplified.

"Alkyl group" is preferably a lower alkyl group, for example, $C_{1-6}$ alkyl groups such as methyl, ethyl, propyl, isopropyl, butyl, isobutyl, sec-butyl, tert-butyl, pentyl and hexyl are used.

"Alkenyl group" is preferably a lower alkenyl group, for example, $C_{2-6}$ alkenyl groups such as vinyl, allyl, isopropenyl, butenyl and isobutenyl are used.

"Alkynyl group" is preferably a lower alkynyl groups, for example, $C_{2-6}$ alkynyl groups such as ethynyl, propargyl and 1-propynyl are used.

"Cycloalkyl group" is preferably a lower cycloalkyl group, for example, $C_{3-6}$ cycloalkyl groups such as cyclopropyl, cyclobutyl, cyclopentyl and cyclohexyl are used.

"Aryl group" is preferably $C_{6-14}$ aryl groups such as phenyl, 1-naphthyl, 2-naphthyl, biphenylyl, 2-indenyl and 2-anthryl. Among others, a phenyl group, for example, is preferably used.

Examples of the substituents, which "hydrocarbon group" of "optionally substituted hydrocarbon group" may optionally have, include halogens (e.g. fluorine, chlorine, bromine and iodine), nitro group, cyano group, hydroxyl group, a lower alkoxy group (e.g. $C_{1-6}$ alkoxy groups such as methoxy, ethoxy, propoxy, isopropoxy, butoxy, isobutoxy, pentyloxy and hexyloxy), amino group, mono-lower alkylamino group (e.g. mono-$C_{1-6}$ alkylamino group such as methylamino and ethylamino), di-lower alkylamino group (e.g. di-$C_{1-6}$ alkylamino group such as dimethylamino and diethylamino), carboxyl group, lower alkylcarbonyl group ($C_{1-6}$ alkyl-carbonyl group such as acetyl and propionyl), lower alkoxycarbonyl group (e.g. $C_{1-6}$ alkoxycarbonyl group such as methoxycarbonyl, ethoxycarbonyl, propoxycarbonyl and butoxycarbonyl), carbamoyl group, mono-lower alkylcarbamoyl group (e.g. mono-$C_{1-6}$ alkylcarbamoyl group such as methylcarbamoyl and ethylcarbamoyl), di-lower alkylcarbamoyl group (e.g. di-$C_{1-6}$ alkylcarbamoyl group such as dimethylcarbamoyl and diethylcarbamoyl), mono-arylcarbamoyl group (e.g. mono-$C_{6-10}$ arylcarbamoyl group such as phenylcarbamoyl and naphthylcarbamoyl), di-arylcarbamoyl group (e.g. di-$C_{6-10}$ arylcarbamoyl group such as diphenylcarbamoyl and naphthylcarbamoyl), aryl group (e.g. $C_{6-10}$ aryl group such as phenyl and naphthyl) and aryloxy group (e.g. $C_{6-10}$ aryloxy group such as phenyloxy and naphthyloxy).

"Hydrocarbon group" of "optionally substituted hydrocarbon group" may optionally have 1 to 5, preferably 1 to 3, of these substituents at any possible position in the hydrocarbon group. When the number of the substituents is two or more, the substituents may be the same as or different from one another.

"Optionally substituted amino group" represented by $R^2$ means amino group which may optionally have, as the substituents, one or two of the above-mentioned "optionally substituted hydrocarbon group" for example. Preferable examples of the substituents, which this "amino group" may optionally have, include lower alkyl groups (e.g. $C_{1-6}$ alkyl groups such as methyl, ethyl and propyl), lower alkenyl groups (e.g. $C_{2-6}$ alkenyl groups such as 2-propenyl and 2-butenyl), lower alkynyl groups (e.g. $C_{2-6}$ alkynyl groups such as propargyl and 2-butynyl), and lower cycloalkyl groups (e.g. $C_{3-6}$ cycloalkyl groups such as cyclopropyl, cyclobutyl, cyclopentyl and cyclohexyl). The substituents of the lower alkyl, lower alkenyl or lower alkynyl group are, for example, the same 1 to 5 substituents which above-mentioned "hydrocarbon group" may optionally have.

"Substituted hydroxyl group" represented by $R^2$ means the hydroxyl group which have, in place of the hydrogen atom of the hydroxyl group, one "optionally substituted hydrocarbon group" mentioned above. Preferable examples of "substituted hydroxyl group" include hydroxyl group substituted with one optionally substituted lower alkyl group. Examples of the "lower alkyl group" includes $C_{1-6}$ alkyl groups such as methyl, ethyl, propyl, isopropyl, butyl and isobutyl. The substituents which "lower alkyl group" may optionally have is, for example, the same ones as the above-mentioned "hydrocarbon group" may optionally have.

"Lower alkylene group" of "optionally halogenated lower alkylene group" represented by X is a bivalent group derived from an alkane having 1 to 6 carbon atoms by dropping two hydrogen atoms from the formula. Examples of "lower alkylene group" include straight or branched $C_{1-6}$ alkylene groups such as methylene, ethylene, propylene, trimethylene, tetramethylene, pentamethylene, butylene, isobutylene and pentylene. "Lower alkylene group" is preferably a $C_{2-3}$ alkylene group (e.g. ethylene, trimethylene, propylene), more preferably ethylene or propylene. In particular, ethylene is preferable.

"Lower alkylene groups" of "optionally halogenated lower alkylene groups" represented by X may have 1 to 5, preferably 1 to 3, more preferably 1 to 2 halogens at any possible position. Examples of the halogens include fluorine, chlorine, bromine and iodine.

"Substituent" represented by Y includes, for example, halogens (e.g. fluorine, chlorine, bromine and iodine), optionally substituted hydrocarbon groups, optionally substituted amino groups, optionally substituted mercapto groups, hydroxyl group, lower alkoxy groups (e.g. $C_{1-6}$ alkoxy groups such as methoxy, ethoxy, propoxy, isopropoxy, butoxy, isobutoxy, pentyloxy and hexyloxy), amide group (e.g. $C_{1-6}$ acylamino groups, preferably $C_{2-6}$ alkanoylamino groups, such as acetamide), and lower alkylenedioxy groups (e.g. $C_{1-3}$ alkylenedioxy groups such as methylenedioxy and ethylenedioxy).

"Optionally substituted hydrocarbon group" includes the same groups as the above-mentioned "optionally substituted hydrocarbon group" represented by $R^1$ or $R^2$.

"Optionally substituted amino group" includes the same groups as the above-mentioned "optionally substituted amino group" represented by $R^2$.

"Optionally substituted mercapto group" includes a mercapto group in which the hydrogen atom in the mercapto group is replaced with one "optionally substituted hydrocarbon group" represented by $R^1$ or $R^2$.

"Substituent" represented by Y may be attached to any possible position on the benzene or pyridine ring of the quinoline skeleton. The number of "substituent" is 1 to 6, preferably 1 to 3. When the number of the substituents is two or more, the substituents may be the same or different. When Y is a lower alkylenedioxy group, it preferably forms a ring with the adjacent two carbon atoms.

In the above formula, $R^1$ is preferably a hydrogen atom or an optionally substituted lower alkyl group (e.g. $C_{1-6}$ alkyl groups such as methyl, ethyl, propyl, isopropyl, butyl, isobutyl, sec-butyl and tert-butyl), etc. The "lower alkyl group" has 1 to 5, preferably 1 to 3 substituents (preferably halogen, etc.) which, for example, the above "hydrocarbon group" may have. $R^1$ is more preferably a hydrogen atom or a $C_{1-4}$ alkyl group (e.g. methyl), etc. In particular, a hydrogen atom is preferable.

Preferable examples of "hydrocarbon group" of "optionally substituted hydrocarbon group" represented by $R^2$ include alkyl groups (e.g. $C_{1-6}$ alkyl groups such as methyl, ethyl, propyl and isopropyl), alkenyl groups (e.g. $C_{2-6}$ alkenyl groups such as vinyl and allyl), alkynyl groups (e.g. $C_{2-6}$ alkynyl groups such as ethynyl and propargyl), and cycloalkyl groups (e.g. $C_{3-6}$ cycloalkyl groups such as cyclopropyl, cyclobutyl, cyclopentyl and cyclohexyl). More preferable examples thereof are lower alkyl groups (e.g. $C_{1-6}$ alkyl groups such as methyl), and lower cycloalkyl groups (e.g. $C_{3-6}$ cycloalkyl groups such as cyclopropyl). The "alkyl groups", "alkenyl groups", "alkynyl groups" and "cycloalkyl groups" may have 1 to 5, preferably 1 to 3 substituents (preferably halogen, etc.) which, for example, the above "hydrocarbon groups" may have.

Preferable examples of the substituents of "optionally substituted amino group" represented by $R^2$ include i) optionally substituted lower alkyl groups and ii) optionally substituted aryl groups. The number of the substituents is 1 or 2. The "lower alkyl groups" include, for example, $C_{1-6}$ alkyl groups such as methyl, ethyl, propyl, isopropyl, butyl, isobutyl, sec-butyl and tert-butyl. The "lower alkyl groups" may have 1 to 3 substituents which, for example, the above "hydrocarbon groups" may have. The "aryl groups" include, for example, $C_{6-10}$ aryl groups such as phenyl. The "aryl groups" may have 1 to 5, preferably 1 to 3 substituents which, for example, the above "hydrocarbon groups" may have (preferably halogens such as fluorine and chlorine, $C_{1-6}$ alkoxy groups such methoxy and ethoxy). In particular, "optionally substituted amino group" represented by $R^2$ is preferably a $C_{1-3}$ alkylamino group.

Preferable examples of the substituents of "substituted hydroxyl group" represented by $R^2$ include, for example, optionally substituted lower alkyl groups (e.g. $C_{1-6}$ alkyl groups such as methyl, ethyl, propyl, isopropyl, butyl, isobutyl, sec-butyl and tert-butyl). The "lower alkyl groups" may have 1 to 3 substituents which, for example, the above "hydrocarbon groups" may have. Preferable examples of the "substituted hydroxyl groups" represented by $R^2$ include lower alkoxy groups (e.g. $C_{1-6}$ alkoxy groups such as methoxy, ethoxy, propoxy, isopropoxy and butoxy) which may have 1 to 3 substituents. The substituents of the "lower alkoxy groups" are selected from, for example, the substituents which the above "hydrocarbon groups" may have.

$R^2$ is preferably an optionally substituted hydrocarbon group, more preferably i) an optionally substituted lower alkyl group or ii) an optionally substituted lower cycloalkyl group, etc. Preferable examples of the "lower alkyl groups" include $C_{1-6}$ alkyl groups such as methyl, ethyl, propyl and isopropyl. Preferable examples of the "lower cycloalkyl groups" include $C_{3-6}$ cycloalkyl groups such as cyclopropyl, cyclobutyl, cyclopentyl and cyclohexyl. The "lower alkyl groups" and "lower cycloalkyl groups" may have 1 to 3 substituents which, for example, the above "hydrocarbon group" may have. Preferable examples of $R^2$ include optionally halogenated $C_{1-6}$ alkyl groups and optionally halogenated $C_{3-6}$ cycloalkyl groups. More preferable examples include $C_{1-6}$ alkyl groups optionally having 1 to 3 halogens (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-triflorohexyl) and $C_{3-6}$ cycloalkyl groups (e.g. cyclopropyl, cyclobutyl, cyclopentyl and cyclohexyl).

Y is preferably halogen (e.g. fluorine, chlorine, bromine and iodine), a lower alkyl group (e.g. $C_{1-6}$ alkyl groups such as methyl, ethyl, propyl and butyl), an optionally substituted aryl group, a lower alkoxy group (e.g. $C_{1-6}$ alkoxy groups such as methoxy, ethoxy, propoxy, isopropoxy, butoxy, isobutoxy, pentyloxy and hexyloxy), etc.

The aryl group of the "optionally substituted aryl group" includes, for example, $C_{6-14}$ aryl groups such as phenyl, 1-naphthyl, 2-naphthyl, biphenylyl, 2-indenyl and 2-anthryl. Examples of the substituents which the "optionally substituted aryl group" may have are the substituents which the above "hydrocarbon groups" may have. The aryl group of the "optionally substituted aryl group" may have 1 to 5 substituents described above at any possible position on the aryl group.

Preferably, Y is at the 2-, 3- and/or 6-position of the quinoline ring.

When Y is at the 2-position of the quinoline ring, Y is preferably halogen (e.g. fluorine, chlorine, bromine and iodine), etc.

When Y is at the 3-position of the quinoline ring, Y is preferably a lower alkyl group (e.g. $C_{1-6}$ alkyl groups such as methyl, ethyl, propyl and butyl), an aryl group (e.g. $C_{6-14}$ aryl groups such as phenyl, 4-fluorophenyl, xylyl, 1-naphthyl, 2-naphthyl, biphenylyl, 2-indenyl and 2-anthryl) optionally having 1 to 5 substituents, etc. In particular, a phenyl group is preferable.

When Y is at the 6-position of the quinoline ring, Y is preferably halogen (e.g. fluorine, chlorine, bromine and iodine), a lower alkoxy group (e.g. $C_{1-6}$ alkoxy groups such as methoxy and ethoxy), etc., more preferably a lower ($C_{1-6}$) alkoxy group, in particular, methoxy.

n is preferably 1 to 3.

m is preferably 0.

Preferable examples of the compound (I) of the present invention include a compound of the formula (I) wherein $R^1$ is hydrogen, $R^2$ is an optionally halogenated $C_{1-6}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl) or a $C_{3-6}$ cycloalkyl group (e.g. cyclopropyl, cyclobutyl, cyclopentyl and cyclohexyl), X is a straight or branched $C_{2-3}$ alkylene group (e.g. ethylene, trimethylene and propylene), a hydrogen or halogen (e.g. chlorine) is attached to the 2-position on the quinoline ring, a lower alkoxy group (e.g. a $C_{1-6}$ alkoxy group such as methoxy and ethoxy) is attached to the 6-position on the quinoline ring, n is 2, and m is 0.

Other preferable examples of the compound (I) include a compound the formula:

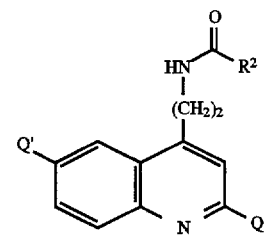

wherein $R^2$ is a $C_{1-6}$ alkyl or $C_{3-6}$ cycloalkyl group optionally substituted by 1 to 3 halogens, Q is hydrogen, halogen, a $C_{6-14}$ aryl group or a $C_{1-6}$ alkoxy group and Q' is a $C_{1-6}$ alkoxy group.

More preferable examples of the compound (I) include a compound of the formula (I) wherein $R^1$ is hydrogen, $R^2$ is an optionally halogenated $C_{1-3}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl and isopropyl), X is an ethylene group, a hydrogen or halogen (e.g. chlorine) is attached to the 2-position on the quinoline ring, a methoxy group is attached to the 6-position on the quinoline ring, n is 2, and m is 0.

Preferable examples of the object compound (I) of the present invention include

N-[2-(2-chloro-6-methoxyquinolin-4-yl)ethyl]acetamide,

N-[2-(6-methoxyquinolin-4-yl)ethyl]acetamide,

N-[2-(2-chloro-6-methoxyquinolin-4-yl)ethyl]-2,2,2-trifluoroacetamide,

N-[2-(6-methoxyquinolin-4-yl)ethyl]-2,2,2-trifluoroacetamide,

N-[2-(2-chloro-6-methoxyquinolin-4-yl)ethyl]propionamide,

N-[2-(6-methoxyquinolin-4-yl)ethyl]propionamide,

N-[2-(2-chloro-6-methoxyquinolin-4-yl)ethyl]cyclopropanecarboxamide,

N-[2-(6-methoxyquinolin-4-yl)ethyl]cyclopropanecarboxamide,

N-[3-(2-chloro-6-methoxyquinolin-4-yl)propyl]acetamide,

N-[3-(6-methoxyquinolin-4-yl)propyl]acetamide,

N-[2-(2-chloro-6-methoxyquinolin-4-yl)propyl]acetamide, and

N-[2-(6-methoxyquinolin-4-yl)propyl]acetamide.

More preferable is

N-[2-(2-chloro-6-methoxyquinolin-4-yl)ethyl]acetamide,

N-[2-(6-methoxyquinolin-4-yl)ethyl]acetamide,

N-[2-(2-chloro-6-methoxyquinolin-4-yl)ethyl]-2,2,2-trifluoroacetamide,

N-[2-(6-methoxyquinolin-4-yl)ethyl]-2,2,2-trifluoroacetamide,

N-[2-(2-chloro-6-methoxyquinolin-4-yl)ethyl]propionamide, and

N-[2-(6-methoxyquinolin-4-yl)ethyl]propionamide.

Examples of the salts of the compound (I) of the invention include pharmaceutically acceptable salts in addition to salts used as synthetic intermediates. Examples of the salts include salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt as well as aluminium salt and ammonium salt. Preferable salts with organic bases include salts with, for example, trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Preferable salts with inorganic acids include salts with, for example, hydrochloric acid, hydrobromic acid, nitric acid, sulfuric acid and phosphoric acid. Preferable salts with organic acids include salts with, for example, formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid, and, when the compound (I) has an acidic functional group, alkali metals such as sodium salt and potassium salt, alkaline earth metal salts such as calcium salt and magnesium salt, ammonium salt.

On the production of the compound (I) or salts thereof of this invention (hereinafter simply referred to as compound (I)), the following description is given.

The compound (I) can be produced by, for example, the following reaction scheme or any process analogous therewith. All symbols of the compounds in the reaction scheme are of the same meaning as defined above. The compounds (Ia), (Ib), (Ic) and (Id) described hereinafter are in the scope of the compound (I).

Reaction Scheme

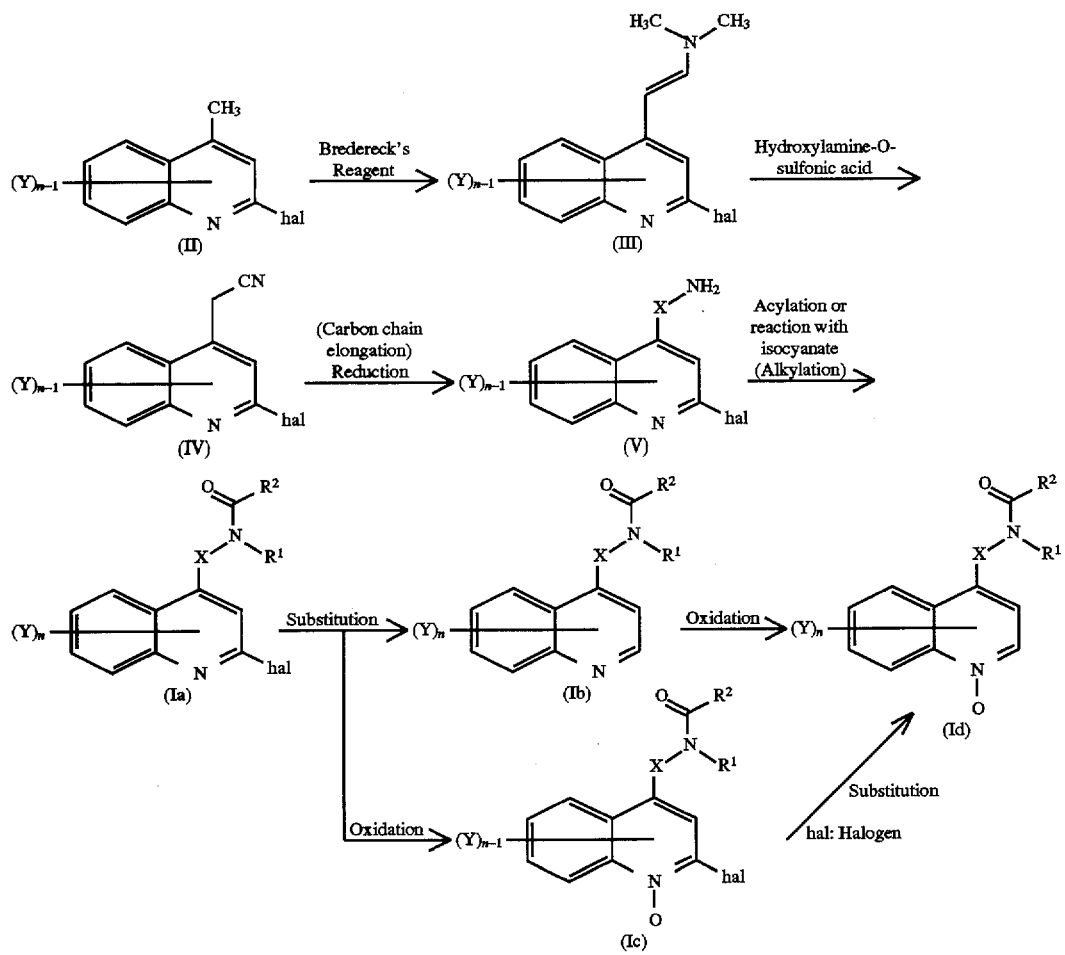

p-toluenesulfonic acid. Preferable salts with basic amino acids include salts with, for example, arginine, lysine and ornithine. Preferable salts with acidic amino acids include salts with, for example, aspartic acid and glutamic acid.

Among them, pharmaceutically acceptable salts are preferable, which are exemplified by, when the compound (I) has a basic functional group, salts with inorganic acids such as hydrochloric acid, hydrobromic acid, nitric acid, sulfuric acid or phosphoric acid, and, salts with organic acids such as acetic acid, phthalic acid, fumaric acid, tartaric acid, maleic acid, citric acid, succinic acid, methanesulfonic acid The compounds (II) to (Id) in the scheme may form salts, including salts of the compound (I) described above.

The compound (II) wherein hal is halogen can be produced by a per se known method, for example, by the methods described in J. Med. Chem., Vol. 16, p. 337 (1973), J. Heterocyclic Chem., Vol. 17, p. 1213 (1980), Croat. Chem. Acta, Vol. 49, p. 517 (1977), Arch, Sci., Vol. 34, p. 89 (1981), J. Med. Chem., Vol. 30, p. 2252 (1987), EP-A-93521, JP-A 58-213761, etc., or a method analogous thereto. The halogens represented by hal include, for example, fluorine, chlorine, bromine and iodine.

The compound (III) can be produced by reacting the compound (II) with Bredereck's reagent (tert-butoxybis- (dimethylamino)methane). The amount of Bredereck's reagent to be used is about 0.5 to 5.0 mol, preferably about 1.0 to 2.0 mol, per mol of the compound (II). It is advantageous that this reaction is conducted in the absence of a solvent or in the presence of an inert solvent. As the solvent, any one can be used so long as it does not hamper the proceeding of the reaction. Examples of the solvents include hydrocarbons such as benzene and toluene, ethers such as tetrahydrofuran, dioxane and 1,2-dimethoxyethane, and amides such as N,N-dimethylformamide and N,N-dimethylacetamide. These solvents can be used alone or as mixtures thereof. The reaction time ranges usually from 1 hour to 30 hours, preferably from 1 hour to 3 hours. The reaction temperature ranges usually from 0° to 200° C., preferably from 40° to 150° C. The product (III) can be isolated from the reaction mixture by conventional methods, and easily purified by conventional methods such as recrystallization.

The compound (IV) can be produced by reacting the compound (III) with hydroxylamine-O-sulfonic acid. The amount of the hydroxylamine-O-sulfonic acid to be used is about 1.0 to 10 mol, preferably about 1.5 to 4.0 mol, per mol of the compound (III). It is advantageous that this reaction is conducted in the presence of an inert solvent. As the solvent, any one can be used so long as it does not hamper the proceeding of the reaction. Examples of the solvents include alcohols such as methanol, ethanol and propanol, amides such as N,N-dimethylformamide and N,N-dimethylacetamide and water, or mixed solvents thereof. The reaction time ranges usually from 1 hour to 100 hours, preferably from 10 hours to 70 hours. The reaction temperature ranges usually from 0° to 200° C., preferably from 10° to 40° C. The product (IV) can be isolated from the reaction mixture by conventional methods, and easily purified by conventional methods such as recrystallization, distillation, chromatography, etc.

The carbon side chain of the compound (IV) can be elongated by per se known methods for elongating carbon chains. For example, after a cyano group is hydrolyzed under alkaline or acidic conditions to a carboxyl group, if necessary, which is then esterified, the carboxyl group or esterified carboxyl group is subjected to reduction to an alcohol, which is then halogenated and cyanided.

The compound (V) can be produced by subjecting the compound (IV) to reduction. The reducing agents to be used include, for example, metal hydrides (e.g. aluminium hydride, diisobutylaluminium hydride), metal hydride complexes (e.g. lithium aluminium hydride, sodium borohydride), Raney nickel catalyst and Raney cobalt catalyst.

The metal hydride is used in an amount of about 1 to 10 mol, preferably about 1 to 3 mol, per mol of the compound (IV). The metal hydride complex is used in an amount of about 1 to 10 mol, preferably about 1 to 3 mol, per mol of the compound (IV). The Raney nickel or Raney cobalt catalyst is used in an amount of about 10 to 1000 w/w %, preferably about 100 to 300 w/w % of the compound (IV). It is advantageous that this reaction is conducted by using an inert solvent. As the solvent, any one can be employed so long as it does not hamper the proceeding of reaction. Preferable examples of the solvents include alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, and organic acids such as formic acid and acetic acid. When a Raney nickel or Raney cobalt catalyst is used, it is preferable, in some instances, to supplement, for example, ammonia to suppress undesirable side reactions. The reaction time ranges usually from 1 hour to 24 hours, preferably from 1 hour to 6 hours, while varying with the activity and amount of the reducing agent then employed. The reaction temperature ranges usually from 0° to 120° C., preferably from 20° to 70° C. The pressure ranges usually from 1 to 100 kgf/cm². The compound (V) can be isolated and refined from the reaction mixture by conventional separating methods, for example, recrystallization, distillation and chromatography.

The compound (Ia) can be produced by subjecting the compound (V) or a salt thereof to acylation. The acylation can be conducted by reacting the compound (V) or a salt thereof with carboxylic acid represented by the formula: $R^2$—COOH wherein $R^2$ is of the same meaning as defined above, or a reactive derivative thereof. Examples of the reactive derivatives of carboxylic acid include acid halogenides (e.g. acid chlorides and acid bromides), acid amides (e.g. acid amides with pyrazole, imidazole or benzotriazole), mixed acid anhydrides (e.g. mono $C_{1-4}$ alkyl-carbonic acid mixed acid anhydrides: monomethylcarbonic acid, monoethylcarbonic acid, monoisopropylcarbonic acid, mono(tert-butyl)carbonic acid, mono($C_{7-10}$ aralkyl)carbonic acid mixed acid anhydrides: monobenzylcarbonic acid, mono(p-nitrobenzyl)carbonic acid, monoallylcarbonic acid, $C_{1-6}$ aliphatic carboxylic acid mixed acid anhydrides: acetic acid, cyanoacetic acid, propionic acid, butyric acid, isobutyric acid, valeric acid, isovaleric acid, pivalic acid, trifluoroacetic acid, trichloroacetic acid, acetoacetic acid, $C_{7-11}$ aromatic carboxylic acid mixed acid anhydrides: benzoic acid, p-toluic acid, p-chlorobenzoic acid, organic sulfonic acid mixed acid anhydrides: methanesulfonic acid, ethanesulfonic acid, benzenesulfonic acid, p-toluenesulfonic acid, etc.), acid azide, activated esters (e.g. diethoxyphosphoric acid esters, diphenoxyphosphoric acid esters, p-nitrophenyl esters, 2,4-dinitrophenyl esters, cyanomethyl esters, pentachlorophenyl esters, esters with N-hydroxysuccinimide, esters with N-hydroxyphthalimide, esters with 1-hydroxybenzotriazolyl, esters with 6-chloro-1-hydroxybenzotriazolyl, esters with 1-hydroxy-1H-2-pyridone, etc.), and activated thioesters (e.g., 2-pyridyl thioesters, 2-benzothiazolyl thioesters, etc.). And, instead of using the reactive derivative, the carboxylic acid or a salt thereof may be allowed to react directly with the compound (V). In this case, it is preferable to allow the reaction to proceed in the presence of a coupling reagent such as N,N'-disubstituted carbodiimides such as N,N'-dicyclohexylcarbodiimide, azolides such as N,N'-carbonyldiimidazole, dehydrating agents such as N-ethoxycarbonyl-2-ethoxy-1,2-dihydroquinoline, phosphorus oxychloride and alkoxyacetylene, and 2-halogenopyridinium salts such as 2-chloropyridiniummethyl iodide and 2-fluoropyridiniummethyl iodide. It is considered that, when the coupling agent is used, the reaction proceeds via the reactive derivative of the carboxylic acid.

The carboxylic acid represented by the formula: $R^2$—COOH wherein $R^2$ is of the same meaning as defined above, is used in an amount ranging usually from about 1 to 5 mol, preferably from about 1 to 2.0 mol, per mol of the compound (V). It is advantageous that this reaction is conducted in the presence of an inert solvent. As the solvent, any one can be used so long as it does not hamper the proceeding of the reaction. Preferable examples of the solvents include ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, halogenated hydrocarbons such as dichloromethane, chloroform, carbon tetrachloride and 1,2-dichloroethane, nitriles such as acetonitrile and propionitrile, and mixed solvents thereof. When an acid halogenide is used as the reactive derivative of the carboxylic acid, it is preferable that an acid-removing agent is previously added to the reaction system to remove the released hydrogen halide from the reaction system. The acid-removing agents include, for example, inorganic bases such as sodium carbonate, potassium carbonate and sodium bicarbonate, aromatic amines such as pyridine and lutidine, and tertiary amines such as triethylamine, tripropylamine, tributylamine, cyclohexyldimethylamine, 4-dimethylaminopyidine, N,N-dimethylaniline, N-methylpiperidine, N-methylpyrrolidine and N-methylmorpholine. While the reaction time varies with the reagent or solvent them employed, it ranges usually from 30 minutes to 24 hours, preferably from 30 minutes to 4 hours. The reaction temperature ranges usually from 0° to 100° C., preferably from 0° to 70° C. The product (Ia) can be isolated from the reaction mixture by conventional methods and easily purified by conventional separating techniques such as recrystallization, distillation and chromatography.

When the compound (Ia) is a urea compound, it is also produced by subjecting the compound (V) to condensation with an isocyanate represented by the formula: $R^{2'}N=C=O$ wherein $R^{2'}$ is a group in which NH is removed from the above-mentioned $R^2$. The amount of the isocyanate is about 1.0 to 5.0 mol, preferably about 1.0 to 2.0 mol, per mol of the compound (V). As the solvent, any one can be used so long as it does not hamper the proceeding of reaction. Preferable examples of the solvent include hydrocarbons such as benzene, toluene, xylene, cyclohexane and hexa ethers such as tetrahydrofuran, dioxane, 1,2-dimethoxyethane, diethyl ether and diisopropyl ether, amides such as N,N-dimethylformamide, N,N-dimethylacetamide and hexamethylphosphoramide, halogenohydrocarbons such as dichloromethane, chloroform, carbon tetrachloride and 1,2-dichloroethane, and ketones such as acetone and methyl ethyl ketone. While the reaction time varies with the reagent and solvent then employed, it ranges usually from 10 minutes to 24 hours, preferably from 10 minutes to 4 hours. The reaction temperature ranges usually from 0° to 100° C., preferably from 0° to 70° C.

When $R^1$ of the compound (Ia) is an alkyl group, the above acylation or condensation with an isocyanate compound is followed by alkylation with the corresponding alkylating agent (e.g. alkyl halides, sulfonic acid esters of alcohols) in the presence of a base. The bases include, for example, alkaline metal hydrides such as sodium hydride and potassium hydride, alkaline metal alkolates such as sodium methylate, sodium ethylate and potassium tert-butoxide, and metal amides such as sodium amide, lithium diisoproylamide and lithium hexamethyldisilazide. The amount of the alkylating agent to be used is about 1 to 3 mol, preferably about 1 to 1.5 mol, per mol of the acyl compound of the compound (V). The amount of the base to be used is about 1 to 3 mol, preferably about 1 to 1.5 mol, per mol of the acyl compound of the compound (V). It is advantageous that this reaction is conducted by using an inert solvent. As the solvent, any one can be used so long as it does not hamper the proceeding of the reaction. Examples of the solvents include aromatic hydrocarbons such as benzene and toluene, amides such as N,N-dimethylformamide and hexamethylphosphoric triamide, ethers such as diethyl ether, tetrahydrofuran and 1,2-dimethoxyethane, and sulfoxides such as dimethyl sulfoxide. The reaction time ranges usually from 1 hour to 24 hours, preferably from 1 hours to 6 hours. The reaction temperature ranges usually from 0° to 150° C., preferably from 0° to 100° C.

The compound (Ib) containing a hydrogen atom at the 2-position can be produced by subjecting the compound (Ia) to reduction. The reduction is conducted in the presence of a catalyst for catalytic reduction and hydrogen in the absence of a solvent or in an appropriate solvent. It is preferable that the catalyst is used in an amount of normally about 0.01 to 500 w/w %, preferably about 0.01 to 250 w/w %, per mol of the compound (Ia). The catalysts include palladium-black, palladium-carbon, platinum oxide, platinum black, Raney nickel and Raney cobalt. It is advantageous that this reaction is conducted by using an inert solvent. As the solvent, any one can be used so long as it does not hamper the proceeding of the reaction. Examples of the solvents include water, alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, nitriles such as acetonitrile and propionitrile, esters such as ethyl acetate, organic acids such as formic acid and acetic acid. These solvent can be used alone or as mixed solvent thereof. While the reaction time varies with the activity and amount of the catalyst to be used, it ranges usually from 0.5 hour to 24 hours, preferably from 0.5 hour to 5 hours. The reaction temperature ranges usually from 0° to 120° C., preferably from 10° to 70° C. The product (Ib) can be isolated from the reaction mixture by conventional methods and easily be purified by conventional techniques such as recrystallization, distillation and chromatography. The reaction can be conducted in the presence of a acid-removing agent to remove the released hydrogen halide from the reaction system. The acid-removing agents include, for example, inorganic bases such as sodium carbonate, potassium carbonate and sodium bicarbonate, aromatic amines such as pyridine and lutidine, and tertiary amines such as triethylamine, tripropylamine, tributylamine, cyclohexyldimethylamine, 4-dimethylaminopyidine, N,N-dimethylaniline, N-methylpiperidine, N-methylpyrrolidine and N-methylmorpholine.

The compound (Ib) containing a mono- or di-lower alkylamino group at the 2-position can be produced by reacting the compound (Ia) or a salt thereof with the corresponding amines in the presence of a base. The amount of the amines is about 1.0 to 10 mol, preferably about 1.0 to 5.0 mol, per mol of the compound (Ia).

Examples of the bases include inorganic bases such as alkaline metal carbonates such as sodium carbonate, potassium carbonate, aromatic amines such as pyridine and lutidine, tertiary amines such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine, alkaline metal hydrides such as sodium hydride and potassium hydride, and metal amides such as sodium amide, lithium diisopropylamide and lithium hexamethyldisilazide. The amount of the base to be used is about 1.0 to 10 mol, preferably 1.0 to 5.0 mol, per mol of the compound (Ia). It is advantageous that this reaction is conducted by using an inert solvent. As the solvent, any one can be used so long as it does not hamper the proceeding of the reaction. Examples of the solvents include alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, and halogenated hydrocarbons such as dichloromethane, chloroform, carbon tetrachloride and 1,2-dichloroethane. These solvents can be used alone or as mixtures thereof. The reaction time ranges usually from 1 hour to 24 hours, preferably from 1 hour to 10 hours. The reaction temperature ranges usually −20° to 200° C., preferably from −10° to 100° C. The product (Ib) can be isolated from the reaction mixture by conventional methods and easily be purified by conventional separation techniques such as recrystallization, distillation and chromatography.

The compound (Ib) containing an alkylthio, alkenylthio or alkynylthio group at the 2-position can be produced by reacting the compound (Ia) or a salt thereof with the corresponding thiols in the presence of a base. The amount of the thiols to be used is about 1.0 to 10 mol, preferably about 1.0 to 5.0 mol, per mol of the compound (Ia). The bases include, for example, inorganic bases such as sodium carbonate, potassium carbonate and sodium bicarbonate, aromatic amines such as pyridine and lutidine, tertiary amines such as triethylamine, tripropylamine, tributylamine, cyclohexyldimethylamine, 4-dimethylaminopyidine, N,N-dimethylaniline, N-methylpiperidine, N-methylpyrrolidine and N-methylmorpholine, alkaline metal hydrides such as sodium hydride and potassium hydride, metal alkolates such as sodium methylate, sodium ethylate and potassium tert-butoxide, and metal amides such as sodium amide, lithium diisopropylamide and lithium hexamethyldisilazide. The amount of the base to be used in about 1.0 to 10 mol, preferably about 1.0 to 5.0 mol, per mol of the compound (Ia). It is advantageous that this reaction is conducted by using an inert solvent. As the solvent, any one can be used so long as it does not hamper the reaction. Examples of the solvents include alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, halogenated hydrocarbons such as dichloromethane, chloroform, carbon tetrachloride and 1,2-dichloroethane. These solvents can be used alone or as mixtures thereof. The reaction time ranges usually from 1 hour to 24 hours, preferably from 1 hour to 10 hours. The reaction temperature ranges usually from −20° to 200° C., preferably from −10° to 100° C. The product (Ib) can be isolated from the reaction mixture by conventional methods and easily be purified by conventional separation techniques such as recrystallization, distillation and chromatography.

The compound (Ib) containing an alkoxy group at the 2-position can be produced by reacting the compound (Ia) or a salt thereof with the corresponding alcohol derivative in the presence of a base. The amount of the alcohol derivative to be used is about 1.0 to 10 mol, preferably about 1.0 to 5.0 mol, per mol of the compound (Ia). The bases include, for example, inorganic bases such as sodium carbonate, potassium carbonate and sodium bicarbonate, aromatic amines such as pyridine and lutidine, tertiary amines such as triethylamine, tripropylamine, tributylamine, cyclohexyldimethylamine, 4-dimethylaminopyidine, N,N-dimethylaniline, N-methylpiperidine, N-methylpyrrolidine and N-methylmorpholine, alkaline metal hydrides such as sodium hydride and potassium hydride, alkaline metal alkolates such as sodium methylate, sodium ethylate and potassium tert-butoxide, and metal amides such as sodium amide and potassium amide, lithium diisopropylamide and lithium hexamethyldisilazide. The amount of the base to be used is about 1.0 to 10 mol, preferably about 1.0 to 5.0 mol, per mol of the compound (Ia). It is advantageous that this reaction is conducted by using an inert solvent. As the solvent, any one can be used so long as it does not hamper the proceeding of the reaction. Examples of the solvents include alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, and halogenated hydrocarbons such as dichloromethane, chloroform, carbon tetrachloride and 1,2-dichloroethane. These solvents can be used alone or as mixtures thereof. The reaction time ranges usually from 1 hour to 24 hours, preferably from 1 hour to 10 hours. The reaction temperature ranges usually from −20° to 200° C., preferably from −10° to 100° C. The product (Ib) can be isolated from the reaction mixture by conventional methods and easily be purified by conventional separation techniques such as recrystallization, distillation and chromatography.

The compound (Ib) containing an aryl group at the 2-position can be produced by reacting the compound (Ia) which has a halogen at the 2-position, or salt thereof with the arylboric acid using palladium complex catalyst. The arylboric acids include the corresponding boric acid such as phenylboric acid and the amount of them to be used in about 1 to 10 mol, preferably about 1 to 5 mol, per mol of the compound (Ia). The palladium catalysts include tetrakis-(triphenylphosphonium)palladium and the amount of them to be used is about 0.001 to 1 mol, preferably about 0.01 to 0.1 mol, per mol of the compound (Ia). The bases include inorganic bases such as sodium carbonate, potassium carbonate, sodium phosphate, potassium phosphate and barium hydroxide and the amount of them to be used is about 1 to 10 mol, preferably about 1 to 5 mol, per mol of the compound (Ia). Examples of the solvents include hydrocarbons such as benzene, toluene and cyclohexane, ethers such as tetrahydrofuran, dioxane and diethylether, amide such as N,N-dimethylformamide, N,N-dimethoxyacetamide or mixtures thereof. The reaction time ranges usually from 0.5 to 100 hours, preferably from 1 to 70 hours. The reaction temperature ranges from 0° to 150° C., preferably from 10° to 120° C. The product (Ic) can be isolated from the reaction mixture by conventional methods and easily be purified by conventional separation techniques such as recrystallization, distillation, chromatography, etc.

The compound (Ic) can be produced by subjecting the compound (Ia) to oxidation. The oxidizing agents to be used include, for example, m-chloroperbenzoic acid, hydrogen peroxide, peracetic acid, m-periodate, acyl nitrate and dinitrogen tetraoxide. The amount of the oxidizing agent to be used is normally about 1 to 5 mol, preferably about 1 to 2.0 mol, per mol of the compound (Ia). It is advantageous that this reaction is conducted by using an inert solvent. As the solvent, any one can be used so long as it does not hamper the proceeding of the reaction. Examples of the solvents include alcohols such as methanol, ethanol and propanol, hydrocarbons such as benzene, toluene and cyclohexane, and halogenated hydrocarbons such as dichloromethane, chloroform, carbon tetrachloride and 1,2-dichloroethane. These solvents can be used alone or as mixtures thereof. While the reaction time varies with the activity and amount of the oxidizing agent to be used, it ranges usually from 0.5 hour to 24 hours, preferably from 0.5 hour to 5 hours. The reaction temperature ranges usually from 0° to 120° C., preferably from 10° to 100° C. The product (Ic) can be isolated from the reaction mixture by conventional methods and easily be purified by conventional separation techniques such as recrystallization, distillation, chromatography, etc.

The compound (Id) containing a hydrogen atom, an alkoxy group, a mono- or di-lower alkyl amino group, halogen (e.g. chlorine) can be produced from the compound (Ib) under the same oxidization conditions as those for the production of the compound (Ic).

The compound (Id) containing an alkylthio, alkenylthio or alkynylthio group at the 2-position can be produced from the compound (Ic) under the same substitution conditions as those for the production of the compound (Ib).

Referring to the configurational isomers (E- and Z-isomers) of each compound described above, when such isomerization takes place, the isomers can be isolated and purified by conventional separating methods such as extraction, recrystallization, distillation and chromatography to give pure compounds. And, in accordance with the methods described in "Shin Jikken Kagaku Koza" 14 (compiled by The Chemical Society of Japan), pp. 251–253, "Fourth Edition Jikken Kagaku Koza" 19 (compiled by The Chemical Society of Japan), pp. 273–274 and analogous methods thereto, isomerization of the double bond is allowed to proceed by heating, using an acid catalyst, a transition metal complex, a metal catalyst, a radical catalyst, light irradiation or using a strongly basic catalyst to give the corresponding pure isomer.

Incidentally stating, the compound (I) gives rise to stereoisomers depending on the kinds of substituents, and these isomers, singly or as a mixture of them, are included in the present invention.

In any of such cases, when further desired, the compound (I) can be synthesized by deprotection, acylation, alkylation, hydrogenation, oxidation, reduction, carbon chain elongation, substituent-exchange reaction singly or by combination of two or more of them. These reactions can be conducted in accordance with a per se known methods, for example, the methods described in "Shin Jikken Kagaku Koza" 14 and 15 (compiled by The Chemical Society of Japan and published in 1977 and 1978).

In each of the reactions described above, when the starting compound has amino group, carboxyl group or hydroxyl group sa a substituent, these groups may be protected with a protective group generally used in the field of peptide chemistry. After completion of the reaction, these protective groups may be removed depending on necessity to give the object compound.

Examples of amino-protective groups include formyl, $C_{1-6}$ alkyl-carbonyl (e.g. acetyl and ethylcarbonyl), $C_{1-6}$ alkyloxycarbonyl (e.g. methoxycarbonyl and ethoxycarbonyl), benzoyl, $C_{7-10}$ aralkyl-carbonyl (e.g. benzylcarbonyl), trityl, phthaloyl and N,N-dimethylaminomethylene groups. These groups may be substituted by 1 to 3 substituents such as halogens (e.g. fluorine, chlorine, bromine and iodine) and nitro groups.

Examples of carboxyl-protective groups include $C_{1-6}$ alkyl (e.g. methyl, ethyl, propyl, isopropyl, butyl and tert-butyl), phenyl, trityl and silyl groups. These groups may be substituted by 1 to 3 substituents such as halogens (e.g. fluorine, chlorine, bromine and iodine), formyl, $C_{1-6}$ alkyl-carbonyl (e.g. acetyl, propionyl and butylcarbonyl) and nitro groups.

Examples of hydroxyl-protective groups include $C_{1-6}$ alkyl (e.g. methyl, ethyl, propyl, isopropyl, butyl and tert-butyl), phenyl, $C_{7-10}$ aralkyl (e.g. benzyl), $C_{1-6}$ alkyl-carbonyl (e.g. acetyl and propionyl), benzoyl, $C_{7-10}$ aralkyl-carbonyl (e.g. benzylcarbonyl), tetrahydropyranyl, tetrahydrofuranyl and silyl groups. These groups may be substituted by 1 to 3 substituents such as halogens (e.g. fluorine, chlorine, bromine and iodine), $C_{1-6}$ alkyl (e.g. methyl, ethyl and propyl), phenyl, $C_{7-10}$ aralkyl (e.g. benzyl), and nitro groups.

For removing these protective groups, a per se known method or analogous methods thereto are employed. For example, methods using acid, base, ultra-violet ray, hydrazine, phenylhydrazine, sodium N-methyldithiocarbamate, tetrabutylammonium fluoride and palladium acetate or reduction.

The obtained compound (I) of the present invention can be isolated and purified by known techniques such as solvent-extraction, phasic transfer, redistribution, crystallization, recrystallization and chromatography. Although the starting compound of the compound (I) of the present invention or a salt thereof can be isolated or purified by known methods as described above, the reaction mixture can be used as the starting material in the next step without isolation.

In the case where the object compound is obtained in the free form by the above reaction, it may optionally be converted into a corresponding salt by conventional methods, and, in the case where the object compound is obtained as a salt, it can be converted into the free form or any other salt. The obtained compound (I) can be isolated from the reaction mixture and purified by conventional methods such as phasic transfer, concentration, solvent-extraction, fractional distillation, crystallization, recrystallization and chromatography.

Additionally, where the compound (I) is present as, for example, configurational isomer, diastereomer or conformers, they can be isolated, when desired, respectively by the above-mentioned isolation and purification means. And, when the compound (I) is a racemic compound, it can be resolved into d-isomer and l-isomer by a conventional means for optical resolution.

The compound of the formula:

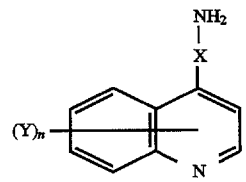

wherein all symbols are as defined above, or a salt thereof obtained during the above process producing the compound (I) is also a novel compound and can be used as the starting compound for the production of the compound of the invention.

The compound (I) acts, as a melatonin agonist, in mammals (e.g. mouse, rat, hamster, rabbit, cat, dog, cow, sheep, monkey and man), and, therefore, can be used as a pharmaceutical composition having a binding affinity to the melatonin receptor, especially, melatonin agonist, for the therapy of diseases possibly affected by melatonin, for example, sleep-awake rhythm disorders, jet lag, abnormal physical conditions caused by a three-shift labor system, seasonal melancholia, disorders in reproduction and neurosecretion, senile dementia including Alzheimer's disease, various accompanied with aging, cerebral circulation disorders, stress, epilepsy, convulsion, anxiety, Parkinsonism, hypertension, glaucoma, cancer, insomnia and diabetes mellitus. In addition, the compound (I) is effective in immunomodulation, nootropic, tranquilizer, or ovulation modulation (e.g. contraception). Especially the compound (I) can be used as a therapeutic agent for insomnia and circadian rhythm disturbance including sleep-awake rhythm disturbance (e.g. insomnia of shift workers) and time zone change syndrome (jet lag).

The compound (I) shows a high affinity for the melatonin receptor, and is less in toxicity and undesirable side effects, which is thus useful as a medicine.

The compound (I) or a salt thereof can be safely administered orally or non-orally (e.g. topically, rectally or by injection, including intramuscularly, subcutaneously and intravenously) as it is or as medicinal preparations mixed with a pharmaceutically acceptable carriers in accordance with a per se known method, for example, tablets (including sugar-coated tablets and film-coated tablets), powdery preparations, granular preparations, capsules (containing soft-capsules), liquid preparations, injectable preparations, suppository preparations, sustained release preparations, plasters and chewing gum.

The amount of the compound (I) or a salt thereof in the composition of the present invention is about 0.01 to nearly 100 w/w %. The daily dose varies with, for example, the subject to be administered, administration routes and diseases to be treated, and, it is preferable, when administration to, for example, an adult patient suffering from sleep disorders, to administer once daily or severally divided dosages in an amount ranging from about 0.1 mg/kg to 20 mg/kg body weight, preferably from about 0.2 mg/kg to 10 mg/kg body weight, more preferably from about 0.5 mg/kg to 10 mg/kg body weight, in terms of the effective component (the compound (I) of a salt thereof).

The compound (I) or a salt thereof may be used with another active component, for example, benzodiazepine (e.g. triazolam, diazepam, alprazolam and estazolam), regulating agents of sleep rhythm such as fatty acid derivatives (e.g. butoctamide and salts thereof), sleep inducing substances such as cis-9,10-octadecenoamide. The compound (I) or a salt thereof and another active component described above are mixed by per se known methods to prepare a pharmaceutical composition described above.

As pharmaceutically acceptable carriers, various organic or inorganic carriers, which are conventionally employed in the field of formulation of pharmaceutical preparations, can be used, and they are incorporated as excipients, lubricants, binders and disintegrants in solid compositions; and as solvents, solubilizers, suspending agents, isotonizing agents, buffering agents and pain-easing agents in liquid compositions. And, depending on necessity, further additives such as preservatives, anti-oxidants, coloring agent, sweeteners, adsorbents and wetting agents can also be supplemented. Preferable examples of excipients include lactose, sugar, D-mannitol, starch, crystalline cellulose and more volatile silicon dioxide. Preferable examples of lubricants include magnesium stearate, calcium stearate, talc and colloidal silica. Preferable examples of binders include crystalline cellulose, sugar, D-mannitol, dextrin, hydroxypropyl cellulose, hydroxypropylmethyl cellulose, polyvinyl pyrrolidone, starch, sucrose, gelatin, methylcellulose and carboxymethyl cellulose sodium. Preferable examples of disintegrants include starch, carboxymethyl cellulose, carboxymethyl cellulose calcium, cross carmellose sodium, carboxymethyl starch sodium and L-hydroxypropylcellulose. Preferable examples of solvents include water for injection, alcohol, propylene glycol, macrogol, sesame oil, corn oil and olive oil. Preferable examples of solubilizers include polyethylene glycol, propylene glycol, D-mannitol, benzyl benzoate, ethanol, trisaminomethane, cholesterol, triethanolamine, sodium carbonate and sodium citrate. Preferable examples of suspending agents include surfactants such as stearyl triethanolamine, sodium lauryl sulfate, lauryl aminopropionic acid, lecithin, benzalkonium chloride, benzethonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of isotonizing agents include glucose, D-sorbitol, sodium chloride, glycerin and D-mannitol. Preferable examples of buffering agents include buffering solutions such as phosphate, acetate, carbonate and citrate. Preferable examples of pain-easing agents include benzyl alcohol. Preferable examples of preservatives include paraoxybenzoic acid esters, chlorobutanol, benzyl alcohol, phenethyl alcohol, dehydroacetic acid and sorbic acid. Preferable examples of anti-oxidants include sulfites, ascorbic acid and α-tocopherol.

BEST MODE FOR CARRYING OUT THE INVENTION

EXAMPLES

The present invention will be described in further detail by the following Reference Examples, Working Examples and Experimental Examples, but they are mere examples and are not intended by way of limitation upon the scope of this invention, and they may be modified within the range which does not deviate the scope of this invention.

In the following Working Examples, Reference Examples and Experimental Examples, "room temperatures" means normally about 10° C. to 35° C., and percent (%) is percent by weight unless otherwise indicated. Other definitions have the following meanings.

s: singlet d: doublet t: triplet q: quartet m: multiplet br: broad

J: coupling constant

Hz: Hertz $CDCl_3$: deuterochloroform $d_6$-DMSO: (dimethyl sulfoxide)-$d_6$

NMR: proton-nuclear magnetic resonance

Reference Example 1

[2-(2-chloro-6-methoxyquinolin-4-yl)ethenyl] dimethylamine

2-Chloro-6-methoxy-4-methylquinoline (25 g, 0.12 mol) and tert-butoxybis(dimethylamino)methane (Bredereck's reagent) (30 g, 0.17 mol) was stirred under heating at 120° C. for 1.5 hours. After cooling the reaction mixture, the precipitated crystals were washed with diisopropyl ether to obtain the title compound (29.2 g, 92%).

mp: 162°–164° C. NMR ($CDCl_3$) δ: 3.01 (6H,s), 3.94 (3H,s), 5.48 (1H,d, J=13.2Hz), 7.15 (1H,s), 7.16 (1H,d,J= 13.2Hz), 7.29 (1H,s), 7.30 (1H,dd,J=2.8Hz,11.7Hz), 7.83 (1H,d,J=11.7Hz). Elemental Analysis for $C_{14}H_{15}ClN_2O$: Calcd.: C,64.00; H,5.75; N,10.66; Cl,13.49 Found: C,63.84; H,5.64; N,10.44; Cl,13.57

Reference Example 2

(2-Chloro-6-methoxyquinolin-4-yl)acetonitrile

[2-(2-Chloro-6-methoxyquinolin-4-yl)ethenyl]dimethylamine (28.3 g, 0.11 mol) and hydroxylamine-O-sulfonic acid (40.2 g, 0.36 mol) were suspended in water (1.2 L), and the mixture was stirred at room temperature for 70 hours. The reaction mixture was neutralized with an aqueous solution of sodium hydroxide, and the organic materials were extracted with a mixed solvent of 5% methanol/ethyl acetate. The extract was washed with saturated brine and water and dried over anhydrous magnesium sulfate. The solvent was evaporated under reduced pressure. The resulting residue was recrystallized from ethyl acetate to obtain the title compound (19.9 g, 79%).

mp: 182°–184° C. (recrystallized from ethyl acetate) NMR (CDCl$_3$) δ: 3.97 (3H,s), 4.09 (2H,s), 7.00 (1H,d, J=2.6Hz), 7.45 (1H,dd,J=2.6Hz,9.2Hz), 7.52 (1H,s), 7.99 (1H,d,J=9.2Hz). Elemental Analysis for $C_{12}H_9ClN_2O$: Calcd.: C,61.95; H,3.90; N,12.04; Cl,15.24 Found: C,61.80; H,4.00; N,11.75; Cl,15.01

Reference Example 3

2-(2-Chloro-6-methoxyquinolin-4-yl)ethylamine

A saturated ammonia/ethanol solution (40 ml) and Raney cobalt (4 g) were added to a solution of (2-chloro-6-methoxyquinolin-4-yl)acetonitrile (1.0 g, 4.3 mmol) in ethanol (150 ml), and the reaction mixture was stirred under an atmosphere of hydrogen (5 kgf/cm$^2$) at room temperature for 3 hours. The Raney cobalt was filtered off, and then the solvent was evaporated under reduced pressure. The residue was washed with diethyl ether to obtain the title compound (855 mg, 84%).

mp: 244°–247° C. (recrystallized from ethanol) NMR (CDCl$_3$) δ: 2.72 (2H,br s), 3.14–3.37 (4H,m), 3.96 (3H,s), 7.26 (1H,s), 7.30 (1H,d,J=2.6Hz), 7.38 (1H,dd, J=2.6Hz, 9.2Hz), 7.89 (1H,d,J=9.2Hz). Elemental Analysis for $C_{12}H_{13}ClN_2O$: Calcd.: C,60.89; H,5.54; N,11.83; Cl,14.98 Found: C,60.80; H,5.50; N,11.96; Cl,14.68

The chemical structures of the compounds obtained by Reference Examples 1 to 3 are as follows.

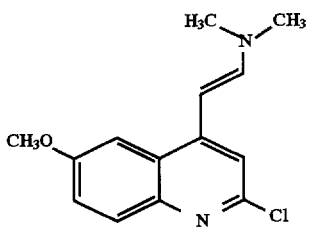

Reference Example 1

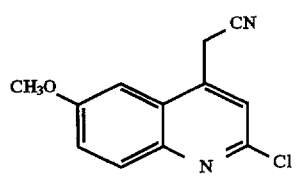

Reference Example 2

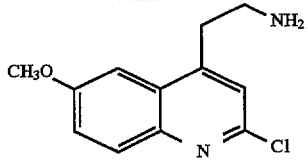

Reference Example 3

Example 1

N-[2-(2-chloro-6-methoxyquinolin-4-yl)ethyl]acetamide

Acetyl chloride (0.37 g, 4.7 mmol) was added dropwise gradually under ice-cooling to a solution of 2-(2-chloro-6-methoxyquinolin-4-yl)ethylamine (1.0 g, 4.2 mmol) and triethylamine (0.87 g, 8.6 mmol) in tetrahydrofuran (50 ml). The reaction mixture was stirred at room temperature for 1 hour and poured into water. The organic materials were extracted with a mixed solvent of 5% methanol/ethyl acetate. The extract was washed with saturated brine and water and dried over anhydrous magnesium sulfate. The solvent was evaporated under reduced pressure. The resulting residue was recrystallized from ethyl acetate to obtain the title compound (0.96 g, 80%).

mp: 162°–164° C. (recrystallized from ethyl acetate) NMR (CDCl$_3$) δ: 2.00 (3H,s), 3.24 (2H,t,J=7.3Hz), 3.60 (2H,q,J=7.3Hz), 4.00 (3H,s), 5.78 (1H,br s), 7.18 (1H,s), 7.37 (1H,dd,J=2.6Hz,9.2Hz), 7.49 (1H,d,J=2.6Hz), 7.90 (1H,d, J=9.2Hz). Elemental Analysis for $C_{14}H_{15}ClN_2O_2$: Calcd.: C,60.33; H,5.42; N,10.05; Cl,12.72 Found: C,60.12; H,5.40; N, 9.94; Cl,12.67

Working Example 2

N-[2-(6-methoxyquinolin-4-yl)ethyl]acetamide

To a solution of N-[2-(2-chloro-6-methoxyquinolin-4-yl)ethyl]acetamide (3.65 g, 13.1 mmol) in ethanol (100 ml) was added 5% palladium carbon (containing water (50%), 9.0 g). The reaction mixture was subjected to catalytic reduction under an atmosphere of hydrogen at atmospheric pressure. After a theoretical amount of hydrogen was added, the palladium carbon was filtered off. The solvent was evaporated under reduced pressure. The resulting residue was purified by column chromatography on silica gel (ethyl acetate:methanol=95:5) to obtain the title compound (2.2 g, 69%).

mp: 113°–115° C. (recrystallized from ethyl acetate) NMR (d$_6$-DMSO) δ: 1.82 (3H,s), 3.17 (2H,t,J=7.1Hz), 3.39 (2H,q,J=7.1Hz), 3.97 (3H,s), 7.32 (1H,d,J=4.4Hz), 7.39 (1H,dd,J=2.6Hz,9.2Hz), 7.78 (1H,d,J=2.6Hz), 7.92 (1H,d, J=9.2Hz), 8.11 (1H,br t,J=5.2Hz), 8.64 (1H,d,J=4.4Hz). Elemental Analysis for $C_{14}H_{16}N_2O_2$: Calcd.: C,68.83; H,6.60; N,11.47 Found: C,68.62; H,6.69; N,11.56

Working Example 3

N-[2-(2-chloro-6-methoxyquinolin-4-yl)ethyl]-2,2,2-trifluoroacetamide

In the same manner as that described in Working Example 1, the title compound was obtained from 2-(2-chloro-6-methoxyquinolin-4-yl)ethylamine and trifluoroacetic anhydride.

Yield: 75% mp: 145°–147° C. (recrystallized from ethyl acetate/hexane) NMR (d$_6$-DMSO) δ: 3.29 (2H,t,J=7.1Hz), 3.58 (2H,q, J=7.1Hz), 3.96 (3H,s), 7.40 (1H,s), 7.46 (1H, dd,J=2.7Hz,9.2Hz), 7.51 (1H,d,J=2.7Hz), 7.87 (1H,d,J= 9.2Hz), 9.61 (1H,br t,J=5.1Hz). Elemental Analysis for C$_{14}$H$_{12}$F$_3$ClN$_2$O$_2$: Calcd.: C,50.54; H,3.64; N,8.42; Cl,10.66; F,17.13 Found: C,50.66; H,3.75; N,8.18; Cl,10.40; F,17.22

Working Example 4

N-[2-(6-methoxyquinolin-4-yl)ethyl]-2,2,2-trifluoroacetamide

In the same manner as that described in Working Example 2, the title compound was obtained from N-[2-(2-chloro-6-methoxyquinolin-4-yl)ethyl]-2,2,2-trifluoroacetamide.

Yield: 79% mp: 172°–174° C. (recrystallized from ethyl acetate) NMR (d$_6$-DMSO) δ: 3.27 (2H,t,J=7.0Hz), 3.57 (2H,q, J=7.0Hz), 3.96 (3H,s), 7.32 (1H,d,J=4.4), 7.40 (1H, dd, J=2.9Hz,8.8Hz), 7.50 (1H,d,J=2.9Hz), 7.93 (1H,d,J=8.8Hz), 8.64 (1H,d,J=4.4Hz), 9.62 (1H,br s). Elemental Analysis for C$_{14}$H$_{13}$F$_3$N$_2$O$_2$: Calcd.: C,56.38; H,4.39; N,9.39; F,19.11 Found: C,56.13; H,4.41; N,9.33; F,19.21

Working Example 5

N-[2-(2-chloro-6-methoxyquinolin-4-yl)ethyl]propionamide

In the same manner as that described in Working Example 1, the title compound was obtained from 2-(2-chloro-6-methoxyquinolin-4-yl)ethylamine and propionyl chloride.

Yield: 83% mp: 173°–175° C. (recrystallized from ethyl acetate) NMR (CDCl$_3$) δ: 1.15 (3H,t,J=7.7Hz), 2.21 (2H,q, J=7.7Hz), 3.24 (2H,t,J=7.3Hz), 3.61 (2H,q,J=7.3Hz), 3.99 (3H,s), 5.72 (1H,br), 7.18 (1H,s), 7.37 (1H,dd,J=2.9Hz, 9.2Hz), 7.46 (1H,d,J=2.9Hz), 7.91 (1H,d,J=9.2Hz). Elemental Analysis: for C$_{15}$H$_{17}$ClN$_2$O$_2$: Calcd.: C,61.54; H,5.85; N,9.57; F,12.11 Found: C,61.37; H,5.97; N,9.43; F,12.00

Working Example 6

N-[2-(6-methoxyquinolin-4-yl)ethyl]propionamide

In the same manner as that described in Working Example 2, the title compound was obtained from N-[2-(2-chloro-6-methoxyquinolin-4-yl)ethyl]propionamide.

Yield: 78% mp: 85°–88° C. (recrystallized from ethyl acetate/hexane) NMR (CDCl$_3$) δ: 1.14 (3H,t,J=7.7Hz), 2.19 (2H,q, J=7.7Hz), 3.26 (2H,t,J=7.3Hz), 3.64 (2H,q,J=7.3Hz), 3.99 (3H,s), 5.73 (1H,br), 7.18 (1H,d,J=4.4Hz), 7.37 (1H, dd,J=2.9Hz,9.2Hz), 7.43 (1H,d,J=2.9H), 8.00 (1H,d,J=9.2Hz), 8.64 (1H,d,J=4.4Hz). Elemental Analysis: for C$_{15}$H$_{18}$N$_2$O$_2$: Calcd.: C,69.74; H,7.02; N,10.84 Found: C,69.62; H,7.13; N,10.53

Working Example 7

N-[2-(2-chloro-6-methoxyquinolin-4-yl)ethyl]cyclopropanecarboxamide

In the same manner as that described in Working Example 1, the title compound was obtained from 2-(2-chloro-6-methoxyquinolin-4-yl)ethylamine and cyclopropanecarbonyl chloride.

Yield: 85% mp: 165°–167° C. (recrystallized from ethyl acetate) NMR (CDCl$_3$) δ: 0.70–0.80 (2H,m), 0.94–1.02 (2H,m), 1.20–1.40 (1H,m), 3.24 (2H,t,J=7.1Hz), 3.64 (2H, q,J=7.1Hz), 3.97 (3H,s), 5.88 (1H,br s), 7.20 (1H,s), 7.33–7.44 (2H,m), 7.91 (1H,d,J=9.2Hz). Elemental Analysis for C$_{16}$H$_{17}$ClN$_2$O$_2$: Calcd.: C,63.05; H,5.62; N,9.19; Cl,11.63 Found: C,62.98; H,5.50; N,9.14; Cl,11.41

Working Example 8

N-[2-(6-methoxyquinolin-4-yl)ethyl]cyclopropanecarboxamide

In the same manner as that described in Working Example 2, the title compound was obtained from N-[2-(2-chloro-6-methoxyquinolin-4-yl)ethyl]cyclopropanecarboxamide.

Yield: 60% mp: 112°–114° C. (recrystallized from ethyl acetate/hexane) NMR (d$_6$-DMSO) δ: 0.57–0.72 (4H,m), 1.45–1.60 (1H,m), 3.18 (2H,t,J=7.2Hz), 3.43 (2H,q,J=7.2Hz), 3.95 (3H,s), 7.32 (1H,d,J=4.4Hz), 7.40 (1H,dd,J=2.7Hz, 9.2Hz), 7.56 (1H,d,J=2.7Hz), 7.93 (1H,d,J=9.2Hz), 8.28 (1H,t,J=5.8Hz), 8.64 (1H,d,J=4.4Hz). Elemental Analysis for C$_{16}$H$_{18}$N$_2$O$_2$: Calcd.: C,71.09; H,6.71; N,10.36 Found C,71.02; H,6.65; N,10.22

Working Example 9

N-[2-(6-methoxy-2-phenylquinolin-4-yl)ethyl]-2,2,2-trifluoroacetamide

A solution of N-[2-(2-chloro-6-methoxyquinolin-4-yl)ethyl]-2,2,2-trifluoroacetamide (0.5 g, 1.5 mmol), tetrakis (triphenylphosphine)palladium (58 mg, 0.05 mmol) and phenylboric acid (0.2 g, 1.65 mmol) in benzene (4.2 ml) was mixed with an aqueous solution (1.9 ml) of sodium carbonate (2 mol). This reaction mixture was heated under reflux in an atmosphere of argon for 64 hours. The reaction mixture was poured into water, and the organic layer was extracted with ethyl acetate. The extract was washed with saturated brine and water and dried over anhydrous magnesium sulfate. The solvent was evaporated under reduced pressure. The resulting residue was purified by column chromatography on silica gel (ethyl acetate:hexane=4:6) to obtain the title compound (515 g, 91%).

mp: 122°–124° C. NMR (CDCl$_3$) δ: 3.37 (2H,t,J=7.0Hz), 3.77 (2H,q, J=7.0Hz), 4.00 (3H,s), 6.62 (1H,br s), 7.36–7.58 (5H,m), 7.65 (1H,s), 8.05–8.15 (3H,m). Elemental Analysis for C$_{20}$H$_{17}$F$_3$N$_2$O$_2$: Calcd.: C,64.17; H,4.58; N,7.48; F,15.22 Found: C,64.07; H,4.68; N,7.31; F,14.92

Working Example 10

N-[2-(6-methoxy-2-phenylquinolin-4-yl)ethyl]propionamide

In the same manner as that described in Working Example 9, the title compound was obtained from N-[2-(2-chloro-6-methoxyquinolin-4-yl)ethyl]propionamide.

Yield: 91% mp: 115°–117° C. NMR (CDCl$_3$) δ: 1.12 (3H,t,J=7.5Hz), 2.17 (2H,q, J=7.5Hz), 3.31 (2H,t,J=6.8Hz), 3.67 (2H,q,J=6.8Hz), 4.00 (3H,s), 5.60 (1H,br s), 7.33–7.57 (5H,m), 7.66 (1H,s), 8.03–8.16 (3H,m). Elemental Analysis for C$_{21}$H$_{22}$N$_2$O$_2$: Calcd.: C,75.42; H,6.63; N,8.38 Found: C,75.20; H,6.58; N,8.18

Working Example 11

N-[2-(6-methoxy-2-phenylquinolin-4-Yl)ethyl]cyclopropanecarboxamide

In the same manner as that described in Working Example 9, the title compound was obtained from N-[2-(2-chloro-6-methoxyquinolin-4-yl)ethyl]cyclopropanecarboxamide.

Yield: 93% mp: 151°–153° C. NMR (CDCl$_3$) δ: 0.65–0.76 (2H,m), 0.91–1.01 (2H,m), 3.33 (2H,t,J=6.6Hz), 3.68 (2H,q,J=6.6Hz), 3.99 (3H,s), 6.62 (1H,br s), 7.31–7.56 (5H,m), 7.70 (1H,s), 8.08–8.16 (3H,m). Elemental Analysis for C$_{22}$H$_{22}$N$_2$O$_2$: Calcd.: C,76.28; H,6.40; N,8.09 Found: C,75.15; H,6.38; N,7.89

Working Example 12

N-[2-(2,6-dimethoxyquinolin-4-yl)ethyl]acetamide

A mixture of N-[2-(2-chloro-6-methoxyquinolin-4-yl) ethyl]acetamide (0.9 g, 3.2 mmol) and sodium methoxide (30 g, 28% methanol solution) in methanol (20 ml) was stirred at 60° C. overnight. The reaction mixture was poured into water, and the organic layer was extracted with ethyl acetate. The extract was washed with saturated brine and water and dried over anhydrous magnesium sulfate. The solvent was evaporated under reduced pressure. The resulting residue was purified by column chromatography on silica gel (ethyl acetate) and recrystallized from a mixed solvent of ethyl acetate and hexane to obtain the title compound (0.46 g, 52%).

mp: 119°–121° C. (recrystallized from ethyl acetate/ hexane) NMR (CDCl$_3$) δ: 1.97 (3H,s), 3.17 (2H,t,J=7.1Hz), 3.61 (2H,q,J=7.1Hz), 3.95 (3H,s), 4.03 (3H,s), 5.64 (1H,br s), 6.73 (1H,s), 7.29 (1H,dd,J=2.9Hz,9.2Hz), 7.38 (1H,d,J= 2.9Hz), 7.78 (1H,d,J=9.2Hz). Elemental Analysis for C$_{15}$H$_{18}$N$_2$O$_3$: Calcd.: C,65.68; H,6.61; N,10.21 Found: C,65.67; H,6.37; N,10.24

The chemical structures of the compounds obtained by Working Examples 1 to 12 are shown in Table 1.

TABLE 1

| Working Example No. | R' | R$^2$ |
|---|---|---|
| 1 | Cl | CH$_3$ |
| 2 | H | CH$_3$ |
| 3 | Cl | CF$_3$ |
| 4 | H | CF$_3$ |
| 5 | Cl | C$_2$H$_5$ |
| 6 | H | C$_2$H$_5$ |
| 7 | Cl | cyclopropyl |
| 8 | H | cyclopropyl |
| 9 | C$_6$H$_5$ | CF$_3$ |
| 10 | C$_6$H$_5$ | C$_2$H$_5$ |
| 11 | C$_6$H$_5$ | cyclopropyl |
| 12 | OCH$_3$ | CH$_3$ |

Formulation Example 1

| (1) Compound of Working Example 1 | 10.0 g |
|---|---|
| (2) Lactose | 60.0 g |
| (3) Corn starch | 35.0 g |
| (4) Gelatin | 3.0 g |
| (5) Magnesium stearate | 2.0 g |

Using 30 ml of a 10 weight % aqueous solution of gelatin (3.0 g in terms of gelatin), a mixture of 10.0 g of the compound produced in Working Example 1, 60.0 g of lactose and 35.0 g of corn starch was granulated through a sieve of 1 mm mesh. The granular product was dried at 40° C., which was sieved again. The granules thus obtained were blended with 2.0 g of magnesium stearate, and the mixture was subjected to compression. The core tablet thus obtained was sugar-coated with an aqueous suspension containing sucrose, titanium dioxide, talc and gum arabic. The coated tablets were polished with bee-wax to prepare 1000 tablets.

Formulation Example 2

| (1) Compound of Working Example 1 | 10.0 g |
|---|---|
| (2) Lactose | 70.0 g |
| (3) Cornstarch | 50.0 g |
| (4) Soluble starch | 7.0 g |
| (5) Magnesium stearate | 3.0 g |

With 70 ml of an aqueous solution of soluble starch (7.0 g in terms of soluble starch), 10.0 g of the compound produced in Working Example 1 and 3.0 g of magnesium stearate were granulated and dried, followed by blending with 70.0 g of lactose and 50.0 g of corn starch. The mixture was subjected to compression to prepare 1000 tablets.

Experimental Example 1

Action of inhibiting 2-[$^{125}$I]iodomelatonin binding

The forebrains of 7-days-old chicken (white leghorn) were homogenized with ice-cold assay buffer (50 mM Tris-HCl, pH 7.7 at 25° C.) and centrifuged at 44,000×g for 10 minutes at 4° C. The pellet was washed once with the same buffer. For the assay, the frozen tissue pellet was thawed and homogenized with the assay buffer to make a protein concentration of 0.3–0.4 mg/ml. In this way, the membrane sample was prepared. The membrane sample was incubated with a test compound and a ligand (80 pM 2-[$^{125}$I]iodomelatonin, about 100,000 dpm) in a total volume of 0.5 ml for 90 minutes at 25° C. The reaction was terminated by adding 3 ml of ice-cold assay buffer immediately followed by vacuum filtration on Whatman GF/B which was further washed twice with 3 ml of ice-cold assay buffer. The radioactivity on the filter was determined by means of γ-counter. Specific binding was calculated by subtracting non-specific binding which was determined in the presence of 10 μM melatonin. The 50% inhibiting concentration (IC$_{50}$) was determined by the log-probit analysis. The results are shown in Table 2.

TABLE 2

Action of inhibiting 2-[$^{125}$I]iodomelatonin binding

| Compounds of working Example | IC$_{50}$ (nM) |
|---|---|
| 1 | 8.4 |
| 3 | 8.9 |

From the results shown in Table 2, it is considered that the compound (I) of the present invention has an excellent melatonin receptor agonistic activity.

INDUSTRIAL APPLICABILITY

The compound (I) or a salt thereof of the present invention shows excellent affinity for a melatonin receptor. Therefore they can provide clinically useful prophylactic and therapeutic agents of diseases related with the action of melatonin in living bodies. In addition, the compound (I) or a salt thereof has excellent pharmacokinetics and water-solubility.

We claim:

1. A di- or tri-cyclic condensed compound of the formula:

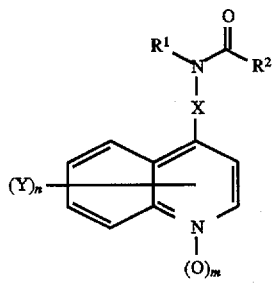

wherein $R^1$ represents hydrogen or an optionally substituted hydrocarbon group provided that $R^1$ is not a cycloalkyl group;

$R^2$ represents an optionally substituted hydrocarbon group, an optionally substituted amino group or a substituted hydroxy group;

X represents an optionally halogenated $C_{2-6}$ alkylene group;

Y represents a substituent;

n represents an integer of 0 to 6; and m represents 0 or 1;

or a salt thereof.

2. A compound of claim 1, wherein $R^1$ is (i) hydrogen or (ii) a $C_{1-6}$ alkyl, $C_{2-6}$ alkenyl, $C_{2-6}$ alkynyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy;

$R^2$ is (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, or (iii) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy;

X is a straight or branched $C_{2-6}$ alkylene group optionally substituted by 1 to 5 halogens; and Y is (i) halogen, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy; (iii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (iv) a mercapto group which may be substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (v) hydroxy, (vi) $C_{1-6}$ alkoxy, (vii) $C_{1-6}$ acylamino or (viii) $C_{1-3}$ alkylenedioxy.

3. A compound of claim 2 wherein X is an ethylene group.

4. A compound of claim 2 wherein $R^2$ is a $C_{1-6}$ alkyl or $C_{3-6}$ cycloalkyl group optionally substituted by 1 to 5 halogens.

5. A compound of claim 1 wherein the 6-position on the quinoline ring is substituted by a $C_{1-6}$ alkoxy group.

6. A compound of claim 2 wherein $R^1$ is hydrogen or $C_{1-6}$ alkyl, $R^2$ is a $C_{1-6}$ alkyl or $C_{3-6}$ cycloalkyl group optionally substituted by 1 to 3 halogens, X is an ethylene group, Y is i) halogen, ii) a $C_{6-14}$ aryl group which may be substituted by 1 to 5 substituents selected from the group consisting of a halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, iii) a $C_{1-6}$ alkoxy group or iv) a $C_{1-6}$ alkyl group, n is an integer of 1 to 3 and m is 0.

7. A compound of claim 1 which is a compound of the formula:

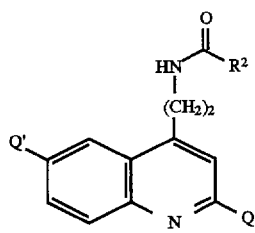

wherein $R^2$ is a $C_{1-6}$ alkyl or $C_{3-6}$ cycloalkyl group optionally substituted by 1 to 3 halogens, Q is hydrogen, halogen, a $C_{6-14}$ aryl group or a $C_{1-6}$ alkoxy group and Q' is a $C_{1-6}$ alkoxy group, or a salt thereof.

8. A compound of claim 1 which is
N-[2-(2-chloro-6-methoxyquinolin-4-yl)ethyl]acetamide,
N-[2-(6-methoxyquinolin-4-yl)ethyl]acetamide,
N-[2-(2-chloro-6-methoxyquinolin-4-yl)ethyl]-2,2,2-trifluoroacetamide,
N-[2-(6-methoxyquinolin-4-yl)ethyl]-2,2,2-trifluoroacetamide,
N-[2-(2-chloro-6-methoxyquinolin-4-yl)ethyl]propionamide,
N-[2-(6-methoxyquinolin-4-yl)ethyl]propionamide, or a salt thereof.

9. A process for producing the compound of claim 1, which comprises subjecting a compound of the formula:

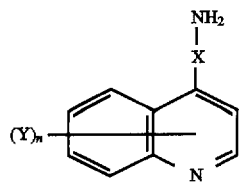

wherein all symbols are as defined in claim 1 or a salt thereof to acylation or reaction with an isocyanate, and if necessary, subjecting the resultant compound to oxidation and/or substituent-exchange reaction.

10. A pharmaceutical composition which comprises a compound of claim 1, if necessary together with a pharmaceutically acceptable carrier.

11. A composition of claim 10 which has a binding affinity for melatonin receptor.

12. A composition of claim 11 which is a regulating agent of circadian rhythm.

13. A composition of claim 11 which is a regulating agent of sleep-awake rhythm.

14. A composition of claim 11 which is a regulating agent of time zone change syndrome.

15. A composition of claim 10 which is a therapeutic agent of sleep disorders.

16. Method for treating disease related to the action of melatonin in mammals which comprises administering to a subject in need a therapeutically effective amount of a compound of claim 1 and a pharmaceutically acceptable carrier.

17. A method for manufacturing a pharmaceutical composition for treating or preventing diseases relating to the action of melatonin in mammals, comprising:

selecting a compound of claim 1; and admixing said compound with a pharmaceutically acceptable carrier.

* * * * *